United States Patent
Dong et al.

(10) Patent No.: US 6,756,201 B2
(45) Date of Patent: *Jun. 29, 2004

(54) DIAGNOSTIC METHODS AND GENE THERAPY USING REAGENTS DERIVED FROM THE HUMAN METASTASIS SUPPRESSOR GENE KAI1

(75) Inventors: Jin-Tang Dong, Cockeysville, MD (US); J. Carl Barrett, Chapel Hill, NC (US); Patricia W. Lamb, Cary, NC (US); John T. Isaacs, Phoenix, MD (US)

(73) Assignees: The United States of America as represented by the Department of Health and Services, Washington, DC (US); John Hopkins University, Baltimore, MD (US)

( * ) Notice: Subject to any disclaimer, the term of this patent is extended or adjusted under 35 U.S.C. 154(b) by 107 days.

This patent is subject to a terminal disclaimer.

(21) Appl. No.: 09/795,380

(22) Filed: Feb. 27, 2001

(65) Prior Publication Data

US 2002/0058257 A1 May 16, 2002

Related U.S. Application Data

(62) Division of application No. 09/232,507, filed on Jan. 15, 1999, which is a division of application No. 08/430,225, filed on Apr. 28, 1995, now Pat. No. 6,204,000.

(51) Int. Cl.[7] .......................... C12Q 1/68; C12P 19/34; G01N 33/574; A61K 49/00
(52) U.S. Cl. ..................... 435/6; 435/91.2; 435/7.23; 424/9.1
(58) Field of Search ................... 435/6, 91.2, 40.52; 424/9.1

(56) References Cited

U.S. PATENT DOCUMENTS 6,204,000 B1 * 3/2001 Dong et al. ............. 435/7.23

OTHER PUBLICATIONS

Dong et al. Proc. of the Amer. Assoc. for Cancer Res., 35:186 (Abstract No. 111), 1994.*
Dong et al. Proc. of the Amer. Assoc. for Cancer Res., 36:105(Abstract No. 630), 1995.*
Dong et al. Proc. of the Amer. Assoc. for Cancer Res., 36:105 (Abstract No. 692), 1995.*
Dong et al., *Proc. of the Ameri. Assoc. for Cancer Res.*, 35:186 (Abstract No. 1111), 1994.
Dong et al., *Proc. of the Ameri. Assoc. for Cancer Res.*, 36:105 (Abstract No. 630), 1995.
Dong et al., *Proc. of the Ameri. Assoc. for Cancer Res.*, 35:692 (Abstract No. 692), 1995.
Adachi et al., *Cancer Res.*, 56(8):1751–55, 1996.
Crystal, *Science*, 270:404–410, 1995.
Deonarain, *Exp. Opin. Ther. Patents*, 8(1):53–69, 1998.
Dong et al., *Science*, 265(5112):884–86, 1995.
Dong et al., *Cancer Res.*, 56:4387–4390, 1996.
Dong et al., *Current Opin. in Oncology*, 9(1):101–7, 1997.
Fukudome et al., *J. Virol.*, 66:1394–1401, 1992.
Gaugitsch et al., *Eur. J. Immunol.*, 21:377–383, 1991.
Gil et al., *J. Immunol.*, 148:2826–2833, 1992.
Ichikawa et al., *Cancer Res.*, 51:3788–3792, 1991.
Ichikawa et al., *Cancer Res.*, 52:3489–3490, 1992.
Imai et al., *J. Immunol.*, 149:2879–2886, 1992.
Mashimo et al., *PNAS of USA*, 95(19):11307–11, 1998.
Miller et al., *FASEB*, 9:190–199, 1995.
Orkin et al., "Report and Recommendations of the Panel to Assess the NIH Investment in Research on Gene Therapy," 1–20, 1995.
Verma et al., *Nature*, 389:239–242, 1997.
Yang et al., *Cancer Letter*, 119(2):149–55, 1997.

* cited by examiner

*Primary Examiner*—Ram R. Shukla
(74) *Attorney, Agent, or Firm*—Klarquist Sparkman, LLP

(57) ABSTRACT

The isolation and characterization of a metastasis tumor suppressor gene KAI1 is disclosed and diagnostic methods and gene therapy approaches utilizing reagents derived from the nucleotide and deduced amino acid sequences of the KAI1 gene are provided.

12 Claims, 4 Drawing Sheets

FIG. 3

```
   1  CCGACTGAGGCACGAGCGGGTGACGCTGGGCCTGCAGCGCGGAGCAGAAAGCAGAACCCG
  61  CAGAGTCCTCCCTGCTGCTGTGTGGACGACACGTGGGCACAGGCAGAAGTGGGCCCTGTG
 121  ACCAGCTGCACTGGTTTCGTGGAAGGAAGCTCCAGGACTGGCGGGATGGGCTCAGCCTGT
   1                                                   M  G  S  A  C
 181  ATCAAAGTCACCAAATACTTTCTCTTCCTCTTCAACTTGATCTTCTTTATCCTGGGCGCA
   6   I  K  V  T  K  Y  F  L  F  L  F  N  L  I  F  F  I  L  G  A
 241  GTGATCCTGGGCTTCGGGGTGTGGATCCTGGCCGACAAGAGCAGTTTCATCTCTGTCCTG
  26   V  I  L  G  F  G  V  W  I  L  A  D  K  S  S  F  I  S  V  L
 301  CAAACCTCCTCCAGCTCGCTTAGGATGGGGGCCTATGTCTTCATCGGCGTGGGGGCAGTC
  46   Q  T  S  S  S  L  R  M  G  A  Y  V  F  I  G  V  G  A  V
 361  ACTATGCTCATGGGCTTCCTGGGCTGCATCGGCGCCGTCAACGAGGTCCGCTGCCTGCTG
  66   T  M  L  M  G  F  L  G  C  I  G  A  V  N  E  V  R  C  L  L
 421  GGGCTGTACTTTGCTTTCCTGCTCCTGATCCTCATTGCCCAGGTGACGGCCGGGGCCCTC
  86   G  L  Y  F  A  F  L  L  L  I  L  I  A  Q  V  T  A  G  A  L
 481  TTCTACTTCAACATGGGCAAGCTGAAGCAGGAGATGGGCGGCATCGTGACTGAGCTCATT
 106   F  Y  F  N  M  G  K  L  K  Q  E  M  G  G  I  V  T  E  L  I
 541  CGAGACTACAACAGCAGTCGCGAGGACAGCCTGCAGGATGCCTGGGACTACGTGCAGGCT
 126   R  D  Y  N  S  S  R  E  D  S  L  Q  D  A  W  D  Y  V  Q  A
 601  CAGGTGAAGTGCTGCGGCTGGGTCAGCTTCTACAACTGGACAGACAACGCTGAGCTCATG
 146   Q  V  K  C  C  G  W  V  S  F  Y  N  W  T  D  N  A  E  L  M
 661  AATCGCCCTGAGGTCACCTACCCCTGTTCCTGCGAAGTCAAGGGGGAAGAGGACAACAGC
 166   N  R  P  E  V  T  Y  P  C  S  C  E  V  K  G  E  E  D  N  S
 721  CTTTCTGTGAGGAAGGGCTTCTGCGAGGCCCCCGGCAACAGGACCCAGAGTGGCAACCAC
 186   L  S  V  R  K  G  F  C  E  A  P  G  N  R  T  Q  S  G  N  H
 781  CCTGAGGACTGGCCTGTGTACCAGGAGGGCTGCATGGAGAAGGTGCAGGCGTGGCTGCAG
 206   P  E  D  W  P  V  Y  Q  E  G  C  M  E  K  V  Q  A  W  L  Q
 841  GAGAACCTGGGCATCATCCTCGGCGTGGGCGTGGGTGTGGCCATCATCGAGCTCCTGGGG
 226   E  N  L  G  I  I  L  G  V  G  V  G  V  A  I  I  E  L  L  G
 901  ATGGTCCTGTCCATCTGCTTGTGCCGGCACGTCCATTCCGAAGACTACAGCAAGGTCCCC
 246   M  V  L  S  I  C  L  C  R  H  V  H  S  E  D  Y  S  K  V  P
 961  AAGTACTGAGGCAGCTGCTATCCCCATCTCCCTGCCTGGCCCCCAACCTCAGGGCTCCCA
 266   K  Y  *
1021  GGGGTCTCCCTGGCTCCCTCCTCCAGGCCTGCCTCCCACTTCACTGCGAAGACCCTCTTG
1081  CCCACCCTGACTGAAAGTAGGGGGCTTTCTGGGGCCTAGCGATCTCTCCTGGCCTATCCG
1141  CTGCCAGCCTTGAGCCCTGGCTGTTCTGTGGTTCCTCTGCTCACCGCCCATCAGGGTTCT
1201  CTTATCAACTCAGAGAAAAATGCTCCCCACAGCGTCCCTGGCGCAGGTGGGCTGGACTTC
1261  TACCTGCCCTCAAGGGTGTGTATATTGTATAGGGGCAACTGTATGAAAAATTGGGGAGGA
1321  GGGGGCCGGGCGCGGTGCTCACGCCTGTAATCCCAGCACTTTGGGAGGCCGAGGCGGGTG
1381  GATCACGAGGTCAGGAGATCGAGACCATCCTGGCTAACATGGTGAAACCCCGTCTCTACT
1441  AAAAATACAAAAAAAATTTAGCCGGGCGCGGTGGCGGGCACCTGTAGTCCCAGCTACTTG
1501  GGAGGCTGAGGCAGGAGAATGGTGTGAACCCGGGAGCGGAGGTTGCAGTGAGCTGAGATC
1561  GTGCTACTGCACTCCAGCCTGGGGACAGAAAGAGACTCCGTCTCAAAAAAAAAAAAAAAA
1621  AAAA
```

FIG. 4
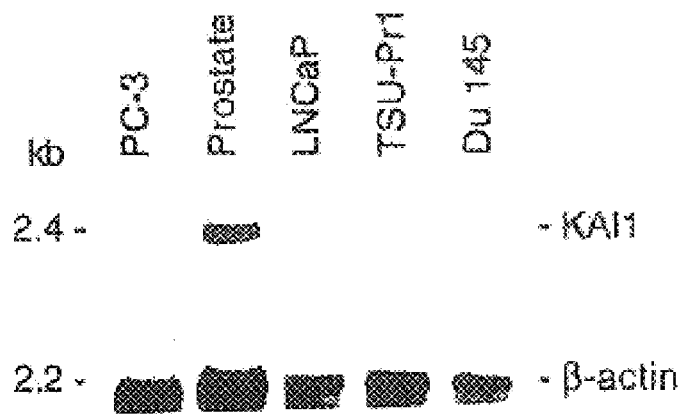
FIG. 5
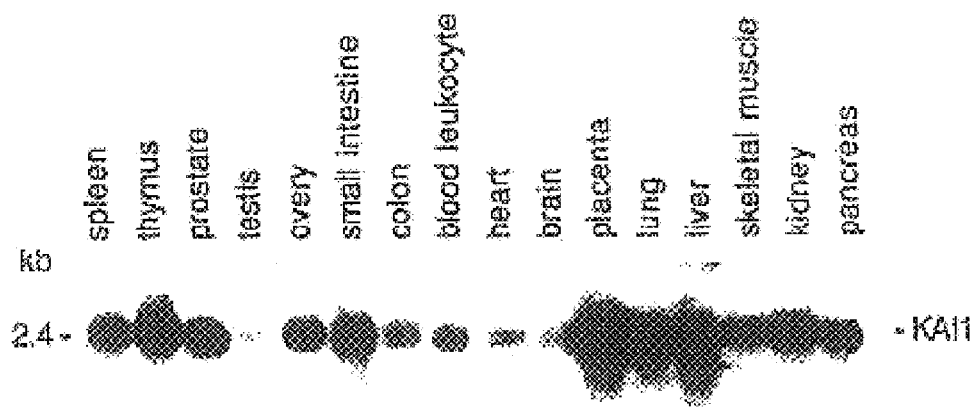

DIAGNOSTIC METHODS AND GENE THERAPY USING REAGENTS DERIVED FROM THE HUMAN METASTASIS SUPPRESSOR GENE KAI1

PRIORITY CLAIM

This application is a divisional of U.S. patent application Ser. No. 09/232,507, filed Jan. 15, 1999, which is a divisional of U.S. patent application Ser. No. 08/430,225, filed Apr. 28, 1995, issued as U.S. Pat. No. 6,204,000.

FIELD OF INVENTION

This invention is in the field of cancer diagnostics and therapeutics. In particular, this invention relates to detection of alterations of wild-type KAI1 gene sequence, KAI1 mRNA and KAI1 protein useful in determining the presence of malignant cancer in a subject or a genetic predisposition to malignancy in a subject. The invention further relates to the use of gene therapy to restore the wild-type KAI1 gene product.

BACKGROUND OF INVENTION

It has been widely accepted that carcinogenesis is a multistep process involving genetic and epigenetic changes that dysregulate molecular control of cell proliferation and differentiation. The genetic changes can include activation of proto-oncogenes and/or the inactivation of tumor suppressor genes that can initiate tumorigenesis as well as lead to the progression of tumors. For example, the tumor suppressor gene p53 may be involved in late stages of colorectal carcinomas (Baker, S. J. et al., (1989) *Science,* 244: 217–221) and a putative metastasis suppressor gene, nm23, was found down-regulated in metastatic tumors versus non-metastatic tumors (Steeg, P. S. et al., (1988) *J. Natl. Canc. Inst.,* 80:200–204). In addition, the activation of ras oncogene and the amplification of N-myc have been associated with progression of human tumors such as breast carcinomas (Liu, E. et al., (1988) *Oncogene* 3:323–327); and neuroblastomas (Brodeur, G. M. et al., (1984) *Science,* 224:1121–1124; Schwab, M. et al., (1984) *Proc. Natl. Acad. Sci. U.S.A.,* 81:4940–4944) but they are unlikely to be universal determinants of tumor progression (Nicolson, G. L. *Bio Essays,* 13:337–342 (1991).

However despite these advances in understanding the genetic changes underlying carcinogenesis, metastasis, which is the main cause of death for most cancer patients (Rosenberg, S. A., Surgical Treatment of Metastasis Cancer (Lippincott, Philadelphia Pa. 1987)), remains one of the most important but least understood aspects of cancer (Liotta, L. A. et al. (1991) *Cell,* 64:327–336; Nicolson, G. L. (1991) *BioEssays,* 13:337–342 and Steeg, P. S. (1992) *Curr. Opin. Oncol.,* 4:134–141). Accordingly, the isolation of metastasis tumor suppressor genes is of great importance for the diagnosis and therapy of cancers.

Cell fusion studies by Ramshaw et al. ((1983) *Int. J. Cancer,* 32:471–478) in which hybridization of non-metastatic and metastatic tumor cells produced cell hybrids which are tumorigenic but no longer metastatic demonstrated the existence of metastasis suppressor genes. More recently, Ichikawa et al. (1991) *Cancer Res.,* 51:3788–3792) demonstrated that the metastatic ability of rat prostatic cancer cells was suppressed when fused to non-metastatic cancer cells and that the reexpression of metastasis was associated with the consistent loss of a normal rat chromosome. A subsequent study using micro-cell-mediated chromosome transfer further mapped a putative human metastasis suppressor gene to the 11p11.2-13 region of human chromosome 11. (Ichikawa et al. (1992 *Cancer Res.,* 52:3486–3490) In this study, these researchers demonstrated that a hybrid retaining human chromosome 11cent-p13 showed a suppression of metastasis while hybrids retaining 11cent-p11.2 did not.

In sum, the data presented in the Ichikawa et al. papers suggested that a putative suppressor gene in the p11.2-13 region of human chromosome 11 may play a role in metastasis. However to date, no gene has been identified in this region which is a candidate metastasis suppressor gene. Thus, there is a need in the art to identify such gene(s) in this chromosome region and to determine if any such gene(s) is associated with metastasis.

SUMMARY OF INVENTION

The present invention relates to methods for detecting alterations of the wild-type KAI1 gene where detection of such alterations is useful in determining the presence of a malignant cancer in a subject or a genetic predisposition to malignancy in a subject. A first method for detecting alterations of the wild-type KAI1 gene comprises analyzing the DNA of a subject for mutations of the KAI1 gene. A second method for detecting alterations of the KAI1 gene comprises analyzing the RNA of a subject for mutations and altered expression of the mRNA product of the KAI1 gene.

The present invention therefore provides nucleic acid probes for detection of alterations of the wild-type KAI1 gene.

The present invention further provides a diagnostic kit containing purified and isolated nucleic acid sequences useful as PCR primers in analyzing RNA or DNA of a subject for alterations of the wild-type KAI1 gene. These PCR primers can also be used to determine the nucleotide sequence of KAI1 alleles.

A third method for detecting alterations of the wild-type KAI1 gene comprises analyzing protein of a subject for alterations in the expression of KAI1 protein.

The invention therefore relates to antibodies to the KAI1 protein and to a diagnostic kit containing antibodies to KAI1 protein useful for detecting alterations in KAI1 protein expression in a subject.

The present invention further provides a method for supplying the wild-type KAI1 gene to a cell having altered expression of the KAI1 protein, the method comprising: introducing a wild-type KAI1 gene into a cell having altered expression of KAI1 protein such that the wild-type gene is expressed in the cell.

FIG. 3 shows the nucleotide (upper line, SEQ ID NO: 19) and deduced amino acid (lower line, SEQ ID NO: 20) sequences of the KAI1 cDNA where the abbreviations for the amino acid residues are:

A, Ala; C, Cys; D, Asp; E, Glu; F, Phe; G, Gly, H, His; I, Ile; K, Lys; L, Leu; M, Met; N, Asn; P, Pro;, Q, Gln; R, Arg; S, Ser; T, Thr; V, Val; W, Trp; Y, Tyr. The four putative transmembrane domains are noted by a dotted underline and the potential N-linked glycosylation sites are doubly underlined.

FIG. 4 shows the results of Northern blot analysis of 15 μg of total RNA isolated from human normal prostate tissue and from cell lines derived from human metastatic prostate cancers. The blot was hybridized sequentially with KAI1 and human β-actin probes.

FIG. 5 shows the results of Northern blot analysis of 2 μg of poly $A^+$ RNA prepared from the various human tissues indicated at the top of FIG. 5. The blot was hybridized sequentially with KAI1 and human β-actin probes.

Figure 6:
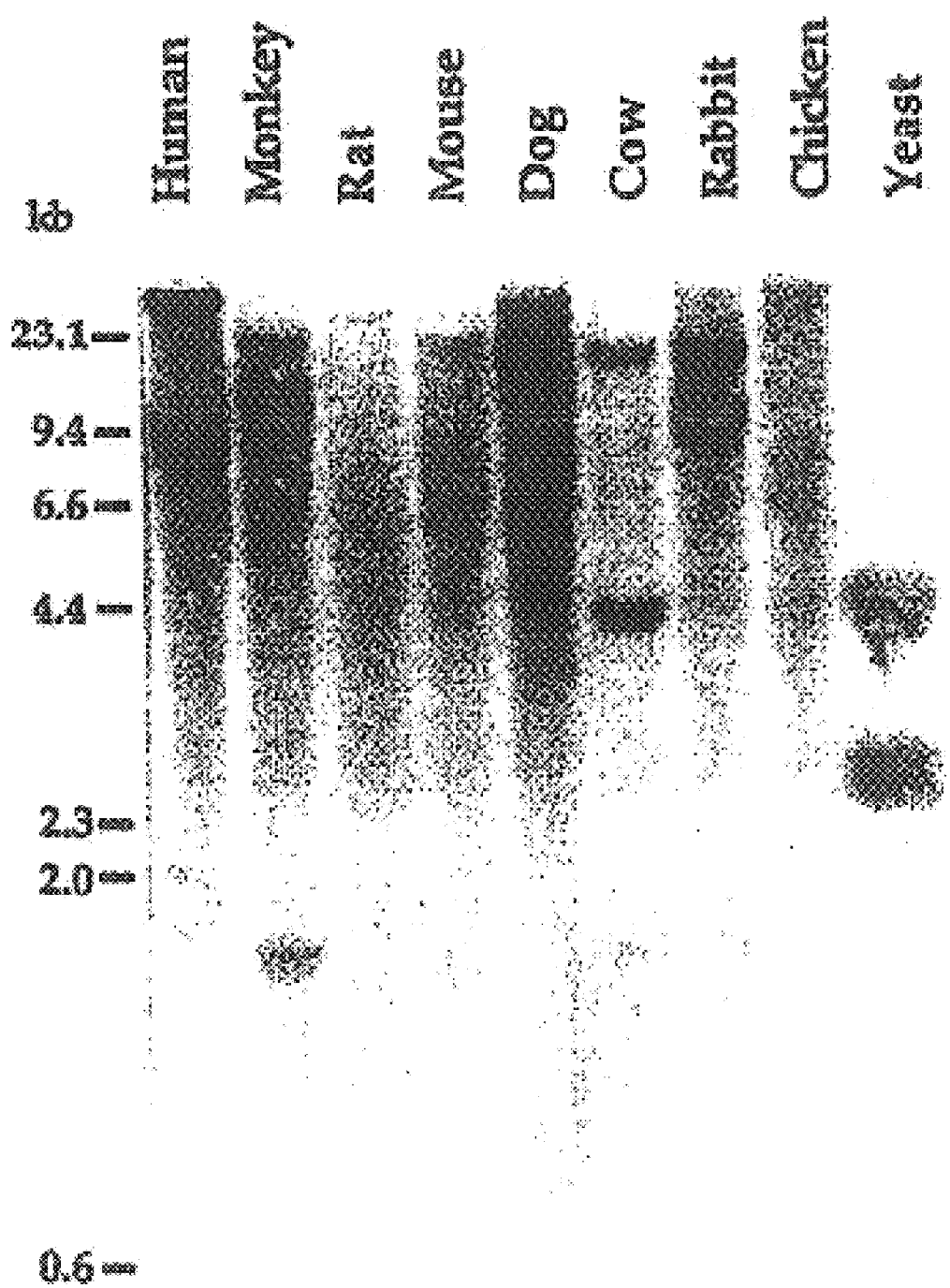

FIG. 6 shows the results of a "zoo" blot of EcoRI-digested genomic DNA of the various species indicated at the top of FIG. 6. The blot was hybridized with KAI1 probe.

DETAILED DESCRIPTION OF INVENTION

The present invention relates to the cloning and characterization of a metastasis suppressor gene on human chromosome 11. The nucleotide and deduced amino acid sequences of this gene, designated KAI1 herein, are shown in FIG. 3. The nucleotide sequence shown in FIG. 3 was cloned from a metastasis suppressed cell hybrid clone AT6.1-11-1* and represents the wild-type KAI1 sequence.

A search of the KAI1 cDNA sequence in GenBank and EMBL databases revealed that the KAI1 cDNA sequence is identical to three cDNA clones from human lymphocytes, designated C33, R2 and IA4 by different laboratories (Imai, T. et al. (1992) *J. Immunol.,* 149, 2879–2886 (1992); Fukudome, K. et al. (1992) *J. Virol.,* 66, 1394–1401 (1992); Gaugitsch, H. W., et al. (1991) *Eur. J. Immunol.,* 21, 377–383 (1991); Gil, M. L. et al. (1992) *J. Immunol.,* 148, 2826–33 (1992)). C33 is associated with the inhibition of virus-induced syncytium formation (Imai, T. et al. (1992); Fukudome, K. et al. (1992)); R2 is strongly up-regulated in mitogen-activated human T cells (Gaugitsch, H. W., et al. (1991)), and IA4 is highly expressed in several B lymphocyte lines (Gil, M. L. et al. (1992)). However, none of these three clones were suggested to function in metastasis and the function of the protein encoded by these clones was not known prior to the present invention.

The present invention further relates to association of alterations of the wild-type KAI1 gene with metastasis. Accordingly, the present invention relates to methods for detecting alterations of the wild-type KAI1 gene in a subject where such methods can provide diagnostic and prognostic information. For example, since loss of expression of the KAI1 gene has been observed in metastatic prostate tumors, these are tumors in which KAI1 has a role in metastasis. Thus, detection of alterations of the wild-type KAI1 gene in a subject may effect the course of treatment chosen by a clinician. In addition, since KAI1 is expressed in all tissues tested including spleen, thymus, prostate, testes, ovary, small intestine, colon, blood leukocyte, heart, brain, placenta, lung, liver, skeletal muscle, kidney and pancreas, alterations of the wild-type KAI1 gene may contribute to metastasis in these tissues.

It is further understood by those of ordinary skill in the art that the methods of the present invention are applicable to any tumor in which alterations of wild-type KAI1 occur. Moreover, the methods of detection disclosed in the present invention can be used prenatally to screen a fetus or presymptomatically to screen a subject at risk of having cancer based on his/her family history. For purposes of the present invention, subject means a mammal.

According to the diagnostic methods of the present invention, alterations of the wild-type KAI1 gene are detected. "Alterations of the wild-type KAI1 gene" as used throughout the specification and claims encompasses mutations of the wild-type KAI1 gene where such mutations include deletions, inversions, insertions, transversions or point mutations of the wild-type KAI1 gene. It is believed that many mutations found in tumor tissues will be those leading to decreased expression of KAI1 protein. However, mutations leading to non-functional gene products can also lead to malignancy. It is further understood that point mutations can occur in regulatory regions (e.g. promoter) or can disrupt proper RNA processing thus leading to loss of expression of the KAI1 gene products respectively.

"Alterations of the wild-type KAI1 gene" as used throughout the specification and claims can also be detected on the basis of altered expression of the wild-type KAI1-specific mRNA and KAI1 protein. The altered expression of these KAI1 gene products may be detected as a loss or reduction in the levels of KAI1 mRNA and protein relative to wild-type levels. Alternatively, the altered expression of KAI1 protein can encompass a loss of function of the KAI1 protein. Those of ordinary skill in the art would therefore understand that altered expression of the KAI1 gene products may be caused by a variety of events, including but not limited to, mutations of the wild-type KAI1 gene, changes in the posttranslational modification of the KAI1 protein (e.g. glycosylation) or loss of a trans-acting factor necessary for transcription of the KAI1 gene.

Provided with the KAI1 cDNA and deduced amino acid sequences shown in FIG. 3, design of particular probes useful in detecting alterations of the wild-type KAI1 gene is well within the skill of the ordinary artisan.

In one embodiment of the invention, the method for detecting alterations of the KAI1 gene comprises analyzing the DNA of a subject for mutations of the wild-type KAI1 gene. For analysis of DNA, a biological specimen is obtained from the subject. Examples of biological specimens that can be obtained for use in the present methods include, but are not limited to, tissue biopsies, whole blood, lymphocytes and tumors. Means for enriching a tissue preparation for tumor cells are known in the art. For example, the tissue may be isolated from paraffin or cryostat sections. Cancer cells may also be separated from normal cells by flow cytometry and other techniques well known in the art. Alternatively, primary cell cultures can be established from tumor biopsies using methods known to those of ordinary skill in the art.

The DNA isolated from the biological specimen can be analyzed for mutations of the wild-type KAI1 gene by a variety of methods including, but not limited to, Southern blotting after digestion with the appropriate restriction enzymes (restriction fragment length polymorphism, RFLP) (Botstein, D. (1980) *Amer. J. Hum. Genet.,* 69:201–205, denaturing gradient electrophoresis technique (Myers, R. M., (1985) *Nature,* 313:495–498), oligonucleotide hybridization (Conner, R. et al., (1984) *EMBO J.*, 3:13321–1326), RNase digestion of a duplex between a probe RNA and the target DNA (Winter, E. et al., (1985) *Proc. Natl. Acad. Sci. U.S.A.*, 82:7575–7579), polymerase chain reaction (PCR) (Saiki, P. K. et al., (1988) *Science*, 239:487–491; U.S. Pat. Nos. 4,683,195 and 4,683,202), ligase chain reaction (LCR) (European Patent Application Nos. 0,320,308 and 0,439,182), and PCR-single stranded conformation analysis (PCR-SSCP) (Orita, M. et al. (1989) *Genomics*, 5:874–879; Dean, M. et al. (1990) *Cell*, 61:863–871).

In one preferred embodiment, Southern blot analysis can be used to examine DNA isolated from a subject for gross rearrangement of the KAI1 gene. The DNA to be analyzed via Southern analysis is digested with one or more restriction enzymes. Following restriction digestion, resultant DNA fragments are separated by gel electrophoresis and the fragments are detected by hybridization with a labelled nucleic acid probe (Southern, E. M. (1975) *J. Mol. Biol.*, 98:503–517).

The nucleic acid sequence used as a probe in Southern analysis can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. 1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:126–131; Erickson, P. F. et al. (1982) *J. of Immunology Methods*, 51:241–249; Matthaei, F. S. et al. (1986) *Anal. Biochem.*, 157:123–128) and methods which allow detection by fluorescence using commercially available products. Each of the nucleic acid sequences used as a probe in Southern analysis is derived from the wild-type KAI1 gene. Preferred probes are derived from having the cDNA sequence shown in FIG. 3.

Once the separated DNA fragments are hybridized to the labelled nucleic acid probes, the restriction digest pattern can be visualized by autoradiography and compared with the restriction digest pattern of the wild-type KAI1 gene. The presence or absence of a restriction fragment length polymorphism (RFLP) in the restriction pattern of the subject's DNA relative to the wild-type restriction pattern indicates an alteration of the wild-type KAI1 gene.

In another preferred embodiment, genomic DNA may be analyzed for mutations in the wild-type KAI1 gene via PCR-SSCP. In this method, each of the pair of primers selected for use in PCR are designed to hybridize with sequences in the wild-type KAI1 gene to permit amplification and subsequent detection of mutations in the denatured amplification product via non-denaturing polyacrylamide gel electrophoresis. In one embodiment, primer pairs are derived from the KAI1 cDNA sequence shown in FIG. 3.

In another embodiment, primer pairs useful in the analysis of genomic DNA mutations of the wild-type KAI1 gene may be derived from intronic sequences which border the 5' and 3' ends of a given exon of the KAI1 gene. Examples of primer pairs permitting specific amplification of specific exons of the KAI1 gene include:

| SEQ ID NO:1: | AGAAGATCAAGTTGAAGAGG |
|---|---|
| SEQ ID NO:2: | GGGACCTCATTTCCTAGCTG |
| SEQ ID NO:3: | ATGAAACTGCTCTTGTCGG |
| SEQ ID NO:4: | TCAGCTCTTGGCTCCCCATT |
| SEQ ID NO:5: | TGGGCACGGGTTTCAGGAAAT |
| SEQ ID NO:6: | TGCAGAGAGCCCCAATGCA |
| SEQ ID NO:7: | AGGGTGAGCCGTGAGCACAA |
| SEQ ID NO:8: | TGCTGAGAGTACCCAGATGC |
| SEQ ID NO:9: | GATGGCCACACCCACGCCC |
| SEQ ID NO:10: | TGCATGGAGAAGGTGCAGGC |
| SEQ ID NO:11: | CCTCTTGCCCACCCTGACTGA |
| SEQ ID NO:12: | TTCACACCATTCTCCTGCCT | where SEQ ID NOS:1 and 2 bound exon 3; SEQ ID NOS:3 and 4 bound exon 4; SEQ ID NOS: 5 and 6 bound exon 6; SEQ ID NOS:7 and 8 bound exon 7; SEQ ID NOS:9 and 10 bound exon 8; and SEQ ID NOS:11 and 12 bound exon 9.

Each primer of a pair is a single-stranded oligonucleotide of about 15 to about 50 base pairs in length which is complementary to a sequence at the 3' end of one of the strands of a double-stranded target sequence. Optimization of the amplification reaction to obtain sufficiently specific hybridization to the KAI1 gene sequence is well within the skill in the art and is preferably achieved by adjusting the annealing temperature. In yet another embodiment, RNA may be analyzed for mutations in the KAI1 gene by RT-PCR-SSCP. In this method, single stranded cDNA is prepared from either total RNA or polyA$^+$-enriched RNA using reverse transcriptase. In this method, each of the pairs of primers selected for use in PCR of the resultant single-stranded cDNA are designed to hybridize with sequences in the KAI1 cDNA which are an appropriate distance apart (at least about 100–300 nucleotides) in the gene to permit amplification and subsequent detection of mutations in the denatured amplification product via non-denaturing polyacrylamide gel electrophoresis. Such primer pairs can be derived from the KAI1 cDNA sequence set forth in FIG. 3. Each pair comprises two such primers, complementary to sequences on each strand separated by generally about 100 to about 300 base pairs.

The primers of this invention can be synthesized using any of the known methods of oligonucleotide synthesis (e.g., the phosphodiester method of Agarwal et al. (1972) *Agnew. Chem. Int. Ed. Engl.*, 11:451, the phosphotriester method of Hsiung et al. (1979). *Nucleic Acids Res.*, 6:1371, or the automated diethylphosphoramidite method of Beuacage et al. (1981). *Tetrahedron Letters*, 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In one embodiment, the primers can be derivatized to include a detectable label suitable for detecting and/or identifying the primer extension products (e.g., biotin, avidin, or radiolabelled dNTP's), or with a substance which aids in the isolation of the products of amplification (e.g. biotin or avidin).

The present invention therefore provides a diagnostic kit for detecting mutations of the KAI1 gene. This diagnostic kit comprises purified and isolated nucleic acid sequences useful as hybridization probes or as PCR primers in analyzing DNA or RNA for alterations of the wild-type KAI1 gene.

In an alternative embodiment, nucleic acid probes can be selected to hybridize to mutant alleles of the KAI1 gene. These allele-specific probes are useful to detect similar mutations in other subjects on the basis of hybridization rather than mismatches. Where such nucleic acid probes are primer pairs which hybridize to mutations in the KAI1 gene sequence, these primer pairs can be used to amplify specific mutant gene sequences present in a biological sample via PCR.

The amplification products of PCR can be detected either directly or indirectly. Direct detection of the amplification products is carried out via labelling of primer pairs. Labels suitable for labelling the primers of the present invention are known to one skilled in the art and include radioactive labels, biotin, avidin, enzymes and fluorescent molecules. The desired labels can be incorporated into the primers prior to performing the amplification reaction. A preferred labelling procedure utilizes radiolabelled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be analyzed for mutations of the KAI1 gene via separating the PCR products by non-denaturing polyacrylamide gel electrophoresis, denaturing polyacrylamide gel electrophoresis (PCR-SSCP) or via direct sequencing of the PCR-products.

In yet another embodiment, unlabelled amplification products can be analyzed for mutations in the KAI1 disease gene via hybridization with nucleic acid probes radioactively labelled or, labelled with biotin, in Southern blots or dot blots. Nucleic acid probes useful in this embodiment are those described earlier for Southern analysis. In a further embodiment, detection of point mutations may be accomplished by molecular cloning of the allele present in the tumor tissue using the cDNA sequence set forth in FIG. 3 and sequencing that allele using techniques well known in the art.

A second method for detecting alterations of the wild-type KAI1 gene comprises analyzing the RNA of a subject for mutations and altered expression of KAI1-specific mRNA.

For the analysis of RNA by this method, RNA can be isolated from, for example, a tumor biopsy sample obtained from said subject where said tumors include, but are not limited to, prostate tumors.

The RNA to be analyzed can be isolated from blood or tumor biopsy samples as whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412).

The methods for analyzing RNA for mutations and altered expression of KAI1-specific mRNA include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), $S_1$ analysis (Sharp, P. A. et al., (1980) Meth. Enzymol., 65:750–768), RNase protection (Sambrook, J. et al. (1989) in "Molecular Cloning, A Laboratory Manual", Cold Spring Harbor Press, Plainview, N.Y.), reverse-transcription polymerase chain reaction (RT-PCR) (Watson, J. D. et al. (1992) in "Recombinant DNA" Second Edition, W. H. Freeman and Company, New York) and RT-PCR-SSCP.

Where expression of KAI1 mRNA is measured, diminished KAI1 mRNA expression is indicative of alteration of the wild-type KAI1 gene. One preferred method for measuring alterations in the level of KAI1-specific mRNA expression is Northern blotting where the nucleic acid sequence used as a probe for detecting KAI1-specific mRNA expression is complementary to all or part of the KAI1 cDNA sequence shown in FIG. 3.

A second preferred method for measuring, alterations in the level of KAI1-specific mRNA expression is detection of KAI1 mRNA expression via hybridization of a nucleic acid probe derived from KAI1 cDNA sequence to RT-PCR products generated from RNA isolated from a biological sample.

A third method for detecting alterations of the wild-type KAI1 gene comprises analyzing the protein of a subject for alteration of wild-type KAI1 protein. In one embodiment, alteration of wild-type KAI1 protein encompasses a loss or reduction in the level of expression of KAI1 protein in a biological sample.

Examples of immunoassays useful in determining the level of expression of KAI1 protein include, but are not limited to, immunoprecipitation, radioimmunoassay, Western blot assay, immunofluorescent assay, enzyme immunoassay, chemiluminescent assay, immunohistochemical assay and enzyme-linked immunosorbent assay (ELISA). In addition, the above immunoassays may be used in combination such as immunoprecipitation followed by Western blot. The above methods are described in *Principles and Practice of Immunoassay*, Price and Newman, eds., Stochton Press, 1991. Such assays may be a direct, indirect, competitive or noncompetitive immunoassay as described in the art (Oelbrick, N. (1984) *J. Clin. Chem. Clin. Biochem.*, 22:895–904). The protein to be analyzed by such methods may be obtained from biological samples such as tumor biopsies and the protein can be obtained as a crude lysate or it can be further purified by methods known to those of ordinary skill in the art including immunoaffinity chromatography using antibodies to the KAI1 protein (Sambrook, J. et al (1989) in "Molecular Cloning: A Laboratory Manual", Cold Spring Harbor Press, Plainview, N.Y.). Alternatively, levels of KAI1 protein may be detected by immunohistochemistry of fixed or frozen tumor sections.

For detection of KAI1 protein by immunoassay, the present invention provides anti-KAI1 antibodies where such antibodies may be polyclonal or monoclonal. If polyclonal antibodies are desired, serum containing polyclonal antibodies to KAI1 protein can be used or the polyclonal antibodies can be purified from other antigens present in the serum by immunoaffinity chromatography. Alternatively, monoclonal antibodies directed against KAI1 can readily be produced by one of ordinary skilled in the art. Methods of producing monoclonal or polyclonal antibodies are known to one of ordinary skilled in the art (Goding, J. W. (1983) monoclonal antibodies: Principles and Practice, Plodermic Press, Inc., NY, N.Y., pp. 56–97; Hurn, B. A. L. et al. (1980) *Meth. Enzymol.*, 70:104–141).

Suitable immunogens which may be used to produce the polyclonal or monoclonal antibodies of the present invention include cell lysate prepared from cells transfected with a recombinant KAI1 protein, partially or substantially purified recombinant or native KAI1 protein, or peptides derived from the KAI1 amino acid sequence shown in FIG. 3. When purification of the recombinant or native KAI1 protein is desired, it can be accomplished by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the KAI1 protein.

In a preferred embodiment, the immunogen is a recombinantly produced KAI1 protein or fragments thereof. Production of recombinant KAI1 protein or a fragment thereof may be directed by a natural or synthetic nucleic acid sequence inserted into a suitable expression vector. A preferred nucleic acid sequence is the KAI1 cDNA sequence shown in FIG. 3. In one embodiment, restriction digest fragments containing the full-length cDNA or fragments thereof containing a coding sequence for KAI1 can be inserted into a suitable expression vector. By suitable expression vector is meant a vector that can function in eukaryotic or prokaryotic cells and is capable of carrying and expressing a nucleic acid sequence encoding the KAI1 protein or a fragment thereof. Such vectors and their use in producing recombinant proteins are known to those of ordinary skill in the art (Sambrook, J. et al. (1989) in "Molecular Cloning, A Laboratory Manual", Cold Spring Harbor Press, Plainview, N.Y.).

The immunogen of the present invention can be used in a suitable diluent such as saline or water, or in complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like. The immunogen may be administered once or at periodic intervals until a significant titer of anti-KAI1 antibody is produced. The antibody may be detected in the serum using an immunoassay.

The antibodies or antigen binding fragments may also be produced by genetic engineering. The technology for expression of both heavy and light chain genes in *E. coli* is the subject of PCT patent applications; publication number WO 901443, WO 901443, and WO 9014424 and in Huse et al. (1989) *Science,* 246:1275–1281.

Alternatively, anti-KAI1 antibodies can be induced by administering anti-idiotype antibodies as immunogens. Conveniently, a purified anti-KAI1 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition.

The composition can be purified as described above for anti-KAI1 antibodies, or by affinity chromatography using anti-KAI1 antibodies bound to the affinity matrix.

In an alternative embodiment, the antibodies of the present invention can be used in situ to detect KAI1 protein in cells or tissues. In one embodiment, the antibodies are used in direct or indirect immunofluorescence. In the direct method, anti-KAI1 antibody labelled with a fluorescent reagent such as fluorescein isothiocyanate, rhodamine B isothiocyanate and the like is reacted directly with the KAI1 present in cells or tissues. In the indirect method, unlabelled anti-KAI1 antibody is reacted with the KAI1 protein present in cells or tissue. The unlabelled anti-KAI1 antibody is then reacted with a labelled second antibody. The second antibody can be labelled with a fluorescent tag as described above. The fluorescently labelled cells or tissues can then be detected using techniques known to one skilled in the art such as a fluorescence-activated cell sorter, light microscopy using a fluorescent light lamp and the like. Alternatively, KAI1 protein can be detected in situ via the use of radio-labelled anti-KAI1 antibody or via the use of an unlabelled anti-KAI1 antibody followed by a radiolabelled second antibody reactive to the anti-KAI1 antibody.

The antibodies of the present invention may also be used to immunoprecipitate the KAI1 protein from a mixture of proteins. The use of immunoprecipitation as a sensitive and specific technique to detect and quantitate target antigen in mixtures of proteins is well known to those of ordinary skill in the art (see Molecular Cloning, A Laboratory Manual, 2d Edition, Maniatis, T. et al. eds. (1989) Cold Spring Harbor Press).

The antibodies of the present invention may also be affixed to solid supports for use in the isolation of KAI1 protein by immunoaffinity chromatography. Techniques for immunoaffinity chromatography are known in the art (Harlow, E. and Lane, D. (1888) "Antibodies: A Laboratory Manual", Cold Spring Harbor Laboratory, Cold Spring Harbor, N.Y.) including techniques for affixing antibodies to solid supports so that they retain their immunoselective activity; the techniques used may be those in which the antibodies are adsorbed to the support as well as those in which the antibodies are covalently linked to the support. Generally, the techniques are similar to those used in covalent linking of antigen to a solid support; however, spacer groups may be included in the bifunctional coupling agents so that the antigen binding site of the antibody remains accessible.

The above described antibodies and antigen binding fragments thereof may be supplied in a diagnostic kit useful for the detection of alterations in the expression of KAI1 protein.

In a second embodiment, alteration of wild-type KAI1 protein encompasses loss of function of the KAI1 protein. The present method therefore includes assays useful in determining the functional status of the KAI protein . For example, since an association between processing of N-linked oligosaccharides and metastatic phenotype has been well-documented (Hakomori, S.-I. (1989) *Advanc. Cancer Res.,* 52:257–331; Dennis, J. W., et al. (1987) *Science,* 236:582–585; Ishikawa, M. et al. (1988) *Cancer Res.,* 48:665–670) it is believed that glycosylation of the KAI1 protein is required for the protein to function as a metastasis suppressor. Thus, detection of a loss of function of KAI1 protein as evidenced by an absence of glycosylation is indicative of the presence of metastatic cancer in a subject.

The present invention also relates to a gene therapy method in which an expression vector containing a nucleic acid sequence representing the wild-type KAI1 gene is administered to a subject having a mutation of the KAI1 gene. A nucleic acid sequence representing wild-type KAI1 gene is that shown in FIG. 3. Such nucleic acid sequence may be inserted into a suitable expression vector by methods known to those of ordinary skill in the art. Expression vectors suitable for producing high efficiency gene transfer in vivo include retroviral, adenoviral and vaccinia viral vectors.

Expression vectors containing a nucleic acid sequence representing wild-type KAI1 gene can be administered intravenously, intramuscularly, subcutaneously, intraperitoneally or orally. A preferred route of administration is intraperitioneally.

Any articles or patents referenced herein are incorporated by reference. The following examples are presented to illustrate various aspects of the invention but are in no way intended to limit the scope thereof.

EXAMPLES

Materials and Methods

Cell lines: AT6.1 is a highly metastatic Dunning rat prostatic cancer cell line. AT6.1–11 clones are microcell hybrids that have a portion of human chromosomes 11 as the sole human genetic materials in AT6.1 cells. Microcell hybrid AT6.1-11-1* contains a fragment of human chromosome 11, cen-p13, from the centromere to region p13, and was suppressed for metastatic ability. Microcell hybrids AT6.1-11-2 and -3 have smaller fragments of human chromosome 11 from the centromere to P11.2 and were not suppressed for metastatic ability. The characteristics and growth condition for these cell lines have been previously described in detail (Ichikawa et al, (1992) *Cancer Res.*, 52:3486–3490). A9-11neo is a mouse A9 cell line containing human chromosome 11pter-q23 (Koi et al, (1989) *Mol Carcinog.*, 2:12–21).

Isolation and Sequencing of KAI1 cDNA clone

Poly (A)+ RNA was isolated from exponentially growing AT6.1-11-1* cells, using a FastTrack mRNA isolation kit (Invitrogen, San Diego, Calif.). Oligo (dT) was used to prime the first strand cDNA synthesis from 5 µg of poly (A)+ RNA. Double-stranded cDNA was cloned into plasmid pSPORT 1 vector by procedures recommended by the vendor (GIBCO BRL, Grand Island, N.Y.). Human Alu sequence primer Alu 559 (Nelson, D. L. et al (189) *Proc. Natl. Acad Sci U.S.A.* 86:6686–6690.) was used to amplify genomic DNA from suppressed hybrid AT6.1-11-1* and the nonsuppressed clone AT6.1-11-2 by PCR. The multiple Alu-PCR fragments of AT6.1-11-1* were cloned into a T-tailed vector pCR1000 (Invitrogen, San Diego, Calif.). Individual clones corresponding to each fragment of Alu-PCR products were isolated after comparing the size of these Alu-PCR products to molecular weight markers in a agarose gel stained with ethidium bromide. Eleven fragments unique to AT6.1-11-1* were labeled by random priming (GIBCO BRL, Bethesda, Md.) and used to screen 5×10$^4$ recombinants of the cDNA library under stringent wash conditions (65° C. in 0.1×SSC+0.1% SDS for 30 min.). Five independent clones were obtained and their inserts were sequenced using the Sequenase kit (US Biochemical, Cleveland, Ohio). DNA sequences were analyzed with the GCG package (version 7.3, 1993, Madison, Wis.).

RNA analysis: Cytoplasmic RNA from AT6.1, AT6.1-11-1*, -2 and -3 were prepared from exponentially growing cells, using FastTrack mRNA isolation kit (Invitrogen, San Diego, Calif.). Other poly (A)+RNA and human multiple tissue Northern blots were purchased from Clontech (Palo Alto, Calif.). 2 µg of poly (A)+RNA was denatured in formamide and fractionated on a 1.2% agarose gel in formaldehyde buffer. The RNA was then transferred onto nylon membrane, baked in an oven at 80° C. for 90 min, and then hybridized with a labeled probe in QuickHyb hybridization solution (Stratagene, La Jolla, Calif.) at 68° C. for 1.5 hours and washed at 68° C. for 30 minutes in 0.1%×SSC, 0.1% SDS and autoradiographed.

DNA analysis: 15 µg of genomic DNA was digested with BamHI and separated on a 1.2% agarose gel. Following denaturation and neutralization, the DNA in the gel was transferred onto nylon membrane. The "zoo" blot containing EcoR1-digested genomic DNA from human, rat, mouse, dog, cow, rabbit, chicken and yeast (Zoo-blot) was purchased from Clontech (Palo Alto, Calif.). The Southern blots were further hybridized and washed under the same conditions as described above for the Northern blots.

PCR: All PCRs in this study were carried out in 50 µl with 25 pmol of each primer, 10 mM Tris.HCl, 500 mM KCl, 1.5 mM MgCl$_2$, 0.01% gelatin, 250 mM of each dNTP and 0.25 units of Taq DNA polymerase (Perkin-Elmer, Norwalk, Conn.). The initial DNA denaturation was performed at 95° C. for 5 min, followed by 35 cycles of 94° C. denaturation for 1 min, 55° C. annealing for 1 min and 72° C. extension of 4 min, with a final extension of 72° C. for 8 min.

Probes and Oligonucleotides sequences: The KAI1 probe (nucleotides 64–1094 of the KAI1 cDNA) used in Southern and Northern blot analyses was generated by PCR with primers shown as SEQ ID NO: 13 AGTCCTCCCTGCT-GCTGTGTG and SEQ ID NO:14 TCAGT-CAGGGTGGGCAAGAGG. Human and rat β-actin probes were PCR products generated by templates and primers purchased from Clontech (Palo Alto, Calif.). The primer sequences for human β-actin are shown as SEQ ID NO:15 GAGGAGCACCCCGTGCTGCTGA and SEQ ID NO:16 CTAGA AGCATTTGCGGTGGACGATGGAGGGGCC and the primer sequences for rat β-actin are shown as SEQ ID NO: 17 TTGTAACCAACTGGGACGATATGG and SEQ ID NO:18 GTCTTGATCTTCATGGTGCTAGG.

Example 1

Cloning of the KAI1 Gene

Figure 1:
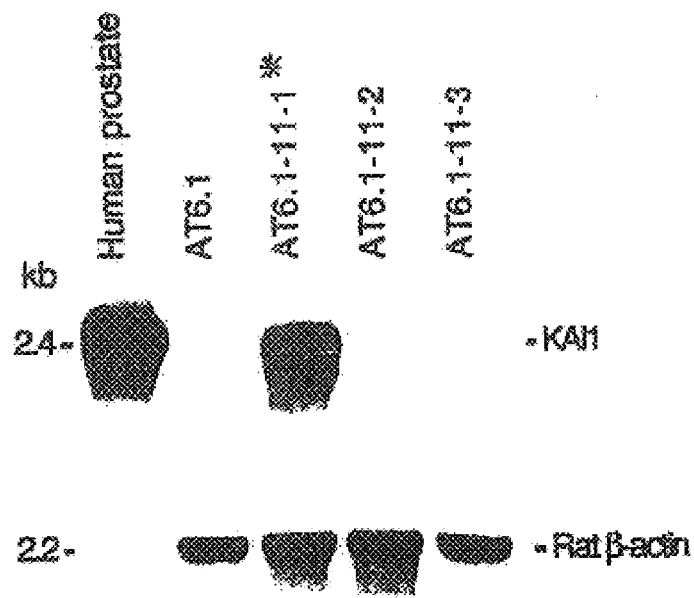
FIG. 1 shows the results of a Northern blot of mRNA from normal tissue (human prostate) and from both metastatic (AT6.1, AT6.1-11-2 and AT6.1-11-3) and non-metastatic (AT6.1-11-1*) tumor cells. 2 $\mu$g of poly A$^+$ RNA per sample was loaded in each lane and the blots were hybridized sequentially with KAI1 cDNA and rat $\beta$-actin probes. The asterisk (*) identifies the hybrid AT6.1-11-1 that contained the 11pcen-p13 region and was suppressed in metastatic ability.

To clone the gene on human chromosome 11 responsible for the metastasis suppression of AT6.1 prostatic cancer cells, genomic DNA fragments from the p11.2-13 region were isolated using human-specific Alu element-mediated PCR (Alu-PCR) (Nelson, D. L. et al *Proc. Natl. Acad. Sci. U.S.A.*, 86:6686–6690) with DNAs from the metastasis suppressed microcell hybrid AT6.1-11-1* and the non-suppressed hybrids AT6.1-11-2 and AT6.1-11-3. The Alu-PCR fragments found only in the AT6.1-11-1 DNA were then used as probes to screen a cDNA library prepared from the suppressed cell hybrid clone AT6.1-11-1* that contains human chromosomal region 11cen-p13. Of five cDNA clones obtained, all were expressed in the suppressed hybrid but not in the nonsuppressed hybrids as detected by reverse transcription-polymerase chain reaction (RT-PCR) using primers derived from these cDNA sequences. Northern analysis of RNA isolated from human prostate and cell lines AT6.1, AT6.1-11-1*, -2 and -3 revealed that two of the cDNA clones detected a 2.4 hb and 4.0 kb transcript respectively in human tissue and the suppressed AT6.1-11-1* cells. The results of a Northern blot for one such clone, designated KAI1 for Kang Ai (Chinese for anti-cancer), are shown in FIG. 1 and clearly demonstrate that KAI1 mRNA was abundant in the metastatic suppressed AT6.1-11-1* cells but absent from the parental AT6.1 cells and the nonsuppressed hybrids. Therefore, the KAI1 clone was analyzed further.

Figure 2:
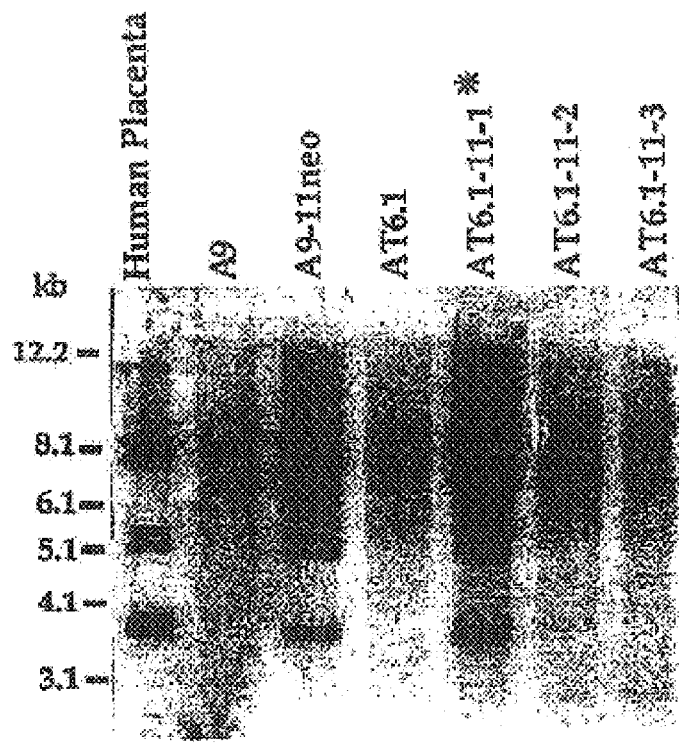
FIG. 2 shows the results of Southern blot analysis of DNA isolated from human placenta, rodent cells (A9 and AT6.1) and human-rodent microcell hybrids (A9-11neo, AT6.1-11-1*, AT6.1-11-2 and AT6.1-11-3). For each sample, 15 $\mu$g of DNA was digested with Hind III, separated on a 1.2% agarose gel and hybridized to a KAI1 cDNA probe. As in FIG. 1, the asterisk (*) identifies the hybrid AT6.1-11-1 that contained the 11pcen-p13 region and was suppressed in metastatic ability.

To confirm that the KAI1 gene was isolated from the p11.2-13 region of human chromosome 11 involved in metastasis suppression, Southern blot analysis was conducted on 15 µg of genomic DNA from human placenta, rodent cells (A9 and AT6.1) and human-rodent microcell hybrids (AT6.1-11-1*, AT6,1-11-2 and AT6.1-11-3), digested with Hind III, separated on a 1.2% agarose gel and hybridized with KAI1 probe. The results shown in FIG. 2 demonstrate that only the cell hybrids that have the p11.2-13 region involved in metastasis suppression (AT6.1-11-1*) have the pattern observed with normal human DNA when hybridized to KAI1 probe. Fluorescence in situ hybridization of a KAI1 probe to metaphase chromosomes further localized KAI1 to the p11.2 region.

Example 2

Nucleotide And Deduced Amino Acid Sequences of the KAI1 cDNA

The nucleotide and deduced amino acid sequences of the KAI1 cDNA are shown in FIG. 3. The KAI1 cDNA has a single open reading frame from nucleotide positions 166 to 966, predicting a protein of 267 amino acids with a calculated molecular weight of 29,610 daltons. An Alu element was present in the 3'-untranslated region of the cDNA. The predicted protein had four hydrophobic and presumably transmembrane domains and one large extracellular hydrophilic domain with three potential N-glycosylation sites. As noted earlier, the KAI1 cDNA sequence is identical to three cDNA clones from human lymphocytes, C33, R2 and IA4.

Example 3

Determination That KAI1 Is A Metastasis Suppressor Gene

To investigate if KAI1 is the gene responsible for metastasis suppression in AT6.1-11-1*, KAI1 cDNA was subcloned into a constitutive expression vector and transfected into parental AT6.1 cells as follows. In brief, KAI1 cDNA was cloned into pCMvneo, in which transcription is driven by the constitutive human cytomegalovirus promoter (Eliyahu, D. et al *Proc Natl Acad Sci U.S.A.*, (1989) 86:8763–8767). The resultant plasmid pCMV-KAI1 was transfected into AT6.1 cells by calcium phosphate precipitate method and the vector alone was also transfected as a negative control. Individual transfectants were isolated in selection medium (RPMI-1640 plus 10% fetal calf serum, 2 units/ml pen-strep and 500 ug/ml neomycin). Exponentially growing untransfected AT6.1, AT6.1-11-1* and AT6.1-11-2 cells and exponentially growing vector (AT6.1VEC-1, AT6.1VEC-2 and AT6.1VEC-3) and KAI1 (AT6.1KAI-1, AT6.1KAI-2 and AT6.1KAI-3) transfectants were collected by scraping and cell clumps were broken up by gentle pipetting. The cell suspension was placed in a tube and allowed to stand at room temperature for 30 min. Cells from the supernatant suspension were collected, washed, and resuspended in cold PBS at $10^6$ cells/ml. Four-to-five-week-old male Ncr nu/nu nude mice (National Cancer Institute Animal Program, Bethesda, Md.) were injected with 0.1 ml of the indicated cell suspension ($10^5$ cells) (the column designated "Clone" in Table 1) subcutaneously at sites on both the right and left midlateral, about ¼ of the distance from the base of the skull to the base of the tail. About 6 weeks after injection, the tumors were weighed and the lungs were inflated with Bouin's solution. Tumor foci on the surface of lungs were scored under a dissecting microscope. Individual transfectants were analyzed for KAI1 expression and for their ability to suppress lung metastases and the results of one experiment are shown in Table 1.

TABLE 1

| Clones | KAI1* mRNA Level | Latency+ (days) | Tumor Age (Days) | Tumor Weight (g) @ Excision | Number of Mice with Metastases | Mean Number± Metastasis Per Mouse Mean (#mice) | P |
|---|---|---|---|---|---|---|---|
| AT6.1 | 0 | 4.3 | 27 | 2.58 | 19/19 | 58(32–135) | |
| AT6.1-11-1* | 10 | 3.7 | 37 | 2.79 | 6/7 | 7(0–9) | <0.005§ |
| AT6.1-11-1-2 | 0 | 4.2 | 37 | 2.78 | 6/6 | 26(20–40) | |
| AT6.1VEC-1 | 0 | 4.9 | 43 | 2.32 | 17/17 | 30(16–57) | |
| AT6.1VEC-2 | 0 | 4.0 | 43 | 3.26 | 17/17 | 30(12–71) | |
| AT6.1VEC-3 | 0 | 5.5 | 43 | 2.57 | 18/18 | 47(15–183) | |
| AT6.1KAI-1 | 10 | 4.2 | 43 | 3.99 | 18/20 | 6(0–14) | <0.001‖ |
| AT6.1KAI-2 | 7 | 4.5 | 41 | 1.79 | 17/19 | 7(0–17) | <0.001‖ |
| AT6.1KAI-3 | 1 | 4.5 | 43 | 2.56 | 18/19 | 23(0–36) | <0.02‖ |

The data shown in this table are from a large, age-matched cohort of "side-by-side" nude mice, with cells inoculated at the same time.
*KAI1 expression was determined by Northern blot analysis. The KAI1 signals on the Northern blot were scored by a densitometer. The value for AT6.1KAI-1 was standardized to 10 and the values for other clones were adjusted accordingly.
+Latency is the time following injection for a palpable tumor to appear.
±The numbers in parentheses indicate the range of metastases in individual mice.
§Compared to the number of metastases with AT6.1-11-2 cells.
‖Compared to the mean number of metastases with all of the three vector transfectants.

The results presented show that expression of KAI1 resulted in a significant suppression of the number of lung metastases per mouse but did not affect the growth rate of the primary tumor. Further, whereas the parental AT6.1 cells yielded 58 metastasis per mouse when injected subcutaneously into nude mice, two transfectants with levels of KAI1 mRNA expression similar to the high level of expression observed in AT6.1-11-1* cells gave only 6 or 7 lung metastases per animal. In contrast, the three vector control transfectants produced 30-47 lung metastases per mouse, which is on average 5.5 times the number of metastases observed with the 2 KAI1 transfectants with high KAI1 mRNA expression (AT6.1KAI-1 and AT6.1KAI-2). In addition, while the AT6.1KAI-3 clone which had low KAI1 expression produced 23 lung metastases, this was still significantly less than the mean number of lung metastases for control transfectants. Finally, Northern analysis showed that KAI1 expression was undetectable or very low in 28 lung metastases from KAI1 transfectants suggesting that selection for cells with absent or reduced KAI1 expression resulted in metastasis formation. These results indicate that the metastatic ability of AT6.1 cells is suppressed by KAI1 expression.

Example 4

KAI mRNA Expression In Cell Lines Derived From Metastatic Human Prostate Tumors

To determine whether KAI1 mRNA expression was reduced in human metastatic prostate tumors relative to expression in normal human prostate, 15 µg total RNA from human normal prostate tissue and from cell lines derived from metastatic prostate cancers (Kaighn, M. E. et al (1979) *Invest. Urol.*:17:16; Horoszewicz, J. J. et al. in Models for Prostate Cancer, G. P. Murphy. Ed. (Alan R. Liss, Inc., New York, 1980). pp 115–132: T. Iizumi. et al. (1987) *J. Urol.* 137:1304, D. D. Mickey et al., in Models for Prostate Cancer. G. P. Murphy. Ed. (Alan R. Liss, Inc. New York, 1980), pp. 67–84) were denatured with formamide, electrophoresed fractionated on a 1.2% agarose gel and hybridized sequentially to KAI1 and human β-actin probes. The results of this Northern blot analysis are shown in FIG. 4 and clearly demonstrate that KAI1 expression was significantly reduced in the human cell lines derived from metastatic prostate tumors (PC-3, LNCaP, TSU-Pr1 and DU145) when compared to normal prostate (prostate). In addition, while longer exposures (4 days at −80 C) of the autoradiogram shown in FIG. 4 (overnite at −80 C) revealed expression of KAI1 mRNA in all of the tumor cells, the level of expression was still much lower than in normal prostate.

To rule out the possibility that the metastasis suppression by KAI1 was due to an indirect immune mechanism, two other experiments were performed. First, parental AT6.1 cells, cell hybrid clone AT6.1-11-1*, or a KAI1 transfectant (AT6.1 KAI-1) were inoculated into the leg of severe combined immune deficient (SCID) mice at $5\times10^5$ cells/mouse. When tumors reached 3–5 $cm^3$, the leg with tumor was surgically removed and animals were followed until 50 to 60 days post inoculation. Lung metastases for each mouse were analyzed as described for Table 1. For AT6.1, 9/9 mice had lung metastases with an average number of 83 per mouse. For AT6.1-11-1*, 4/9 mice had lung metastases with an average number of 6 per mouse. For AT6.1KAI-1, 2/7 mice had lung metastases with an average number of 2 per mouse. These studies demonstrated that even in SCID mice, which are more immune compromised than nude mice, metastasis suppression was observed.

Second, highly metastatic rat mammary cancer cells into which the KAI1 gene was introduced via microcell-mediated chromosome transfer, retained their ability to metastasize (Rinker-Schaefer, C. W. et al. (1994) *Cancer Res.*, 54:6249–6256) even though the hybrids expressed similar level of KAI1 mRNA. Based upon these data, a more direct mechanism appears to be responsible for the metastasis suppression by KAI1. Consistent with this possibility, high KAI1 expressing AT6.1-11-1* hybrid cells have about 50% reduction in their invasive ability as compared to parental AT6.1 cells or nonsuppressed AT6.1-11-2 hybrid cells in Boyden chamber assay. In brief, Boyden chamber invasion assays were performed as described by J. Vukanovic et al. (1993) *Cancer Res.*, 53: 1833), using matrigel coated filters and 5% fetal bovine serum as chemoattractant in the lower well. During the 12 hours of the assay, 19±3 parental AT6.1 cells per high power field invaded through the matrigel filters versus 10±2 for the metastasis suppressed AT6.1-11-1* hybrid cells and 18±2 for the nonsuppressed AT6.1-11-2 hybrid cells.

Example 5

Expression of KAI1 Gene In Human Tissues

To evaluate the expression level of KAI1 gene in various human tissues, Northern analysis was performed on RNA isolated from multiple human tissues. In brief, a human multiple tissue Northern blot purchased from Clontech (Palo Alto, Calif.) was hybridized sequentially with KAI1 and human β-actin probes under conditions described in the Methods section. The results presented in FIG. 5 show that the 2.4 kb KAI1 transcript was detected in all the human tissues tested, with high abundance in prostate, lung, liver, kidney, bone marrow and placenta; moderate abundance in mammary gland, pancreas, skeletal muscle and thymus; and low expression in brain, heart, ovary, stomach and uterus.

Example 6

Conservation Of The KAI1 Gene Across Species

To determine if the KAI1 gene is evolutionarily conserved across species, a zoo blot containing EcoRI-digested genomic DNA from various species was purchased from Clontech (Palo Alto, Calif.) and hybridized with KAI1 probe. The results presented in FIG. 6 show that the evolutionary conservation of KAI1 coding sequence is high in human, monkey, dog and rabbit and moderate in cow, rat, mouse. The evolutionary conservation and wide tissue distribution for KAI1 suggest that the gene may have an essential biological function.

Example 7

Correlation Of Altered KAI1 Expression In Human Tissue Samples With Metastasis

Tumor biopsies of liver metastases from prostate cancer patients and liver biopsies from healthy patients are analyzed for KAI1 mRNA expression by Northern blotting. KAI1 mRNA expression is lost in the tumor samples indicating that the presence of liver metastases in the prostate cancer patients is correlated with altered KAI1 expression.

What is claimed is:

1. A method of detecting an ability of a breast, prostate, or ovarian tumor cell to metastasize, comprising:
comparing the level of KAI1 mRNA in the breast, prostate, or ovarian tumor cell to the level of wild-type KAI1 mRNA in a normal breast, prostate, or ovarian cell to determine the presence of a reduction of expression of KAI1 mRNA, wherein the reduction of expression indicates an ability of the breast, prostate, or ovarian tumor cell to metastasize.

2. A method for determining a prognosis of a breast, prostate, or ovarian tumor in a subject, comprising:
comparing the level of KAI1 mRNA in a cell of the breast, prostate, or ovarian tumor to the level of wild-type KAI1 mRNA in a normal breast, prostate, or ovarian cell to determine a presence of a reduction of expression of KAI1 mRNA, wherein the reduction of expression indicates the prognosis of the breast, prostate, or ovarian tumor in the subject.

3. The method of claim 2, wherein the tumor is a prostate tumor.

4. The method of claim 1, wherein the KAI1 mRNA encodes polypeptide having a sequence as set forth as SEQ ID NO:20.

5. The method of claim 1, wherein comparing the level of KAI1 mRNA in the tumor cell to the level of wild-type KAI1 mRNA in the normal cell comprises Northern blotting, dot hybridization, slot hybridization, filter hybridization, S1 analysis, RNase protection, or reverse-transcription polymerase chain reaction (RT-PCR).

6. The method of claim 5, wherein comparing the level of KAI1 mRNA in the tumor cell to the level of wild-type KAI1 mRNA in the normal cell comprises reverse-transcription on polymerase chain reaction (RT-PCR) or comprises Northern blotting.

7. The method of claim 5, wherein comparing the level of KAI1 mRNA in the tumor cell to the level of wild-type KAI1 mRNA in the normal cell comprises Northern blotting.

8. The method of claim 2, wherein the KAI1 mRNA encodes a polypeptide having a sequence as set forth as SEQ ID NO:20.

9. The method of claim 2, wherein comparing the level of KAI1 mRNA in the cell of the tumor to the level of wild-type KAI1 mRNA in the normal cell comprises Northern blotting, dot hybridization, slot hybridization, filter hybridization, S1 analysis, RNase protection, reverse-transcription polymerase chain reaction (RT-PCR).

10. The method of claim 9, wherein comparing the level of KAI1 mRNA in the cell of the tumor to the level of wild-type KAI1 mRNA in the normal cell comprises reverse-transcription polymerase chain reaction (RT-PCR).

11. The method of claim 9, wherein comparing the level of KAI1 mRNA in the cell of the tumor to the level of wild-type KAI1 mRNA in the normal cell comprises Northern blotting.

12. The method of claim 1, wherein the tumor is a prostate tumor.

* * * * *

UNITED STATES PATENT AND TRADEMARK OFFICE
CERTIFICATE OF CORRECTION

PATENT NO. : 6,756,201 B2
DATED : June 29, 2004
INVENTOR(S) : Dong et al.

It is certified that error appears in the above-identified patent and that said Letters Patent is hereby corrected as shown below:

<u>Title page</u>,
Item [56], References Cited, OTHER PUBLICATIONS, insert -- Rinker-Schaeffer et al., *Cancer Res.*, 54(23):6249-56, 1994 --.

<u>Column 27</u>,
Line 43, "polypeptide" should read -- a polypeptide --.

<u>Column 28</u>,
Line 24, "on polymerase" should read -- or polymerase --.

Signed and Sealed this

Twenty-first Day of June, 2005

JON W. DUDAS
*Director of the United States Patent and Trademark Office*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 1:

AGAAGATCAA GTTGAAGAGG                                         20

(2) INFORMATION FOR SEQ ID NO: 2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 2:

GGGACCTCAT TTCCTAGCTG                                         20

(2) INFORMATION FOR SEQ ID NO: 3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (xi) SEQUENCE DESCRIPTION: SEQ ID NO: 3:

ATGAAACTGC TCTTGTCGG                                          19

(2) INFORMATION FOR SEQ ID NO: 4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 4:

TCAGCTCTTG GCTCCCCATT                                         20

(2) INFORMATION FOR SEQ ID NO: 5:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 5:

TGGGCACGGG TTTCAGGAAA T                                       21

(2) INFORMATION FOR SEQ ID NO: 6:

(i) SEQUENCE CHARACTERISTICS:
       (A) LENGTH: 20 base pairs
       (B) TYPE: nucleic acid
       (C) STRANDEDNESS: single (D) TOPOLOGY: linear (xi) SEQUENCE DESCRIPTION: SEQ ID NO: 6:

TGCAGAGAGC CCCAAATGCA                                                    20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 7:

AGGGTGAGCC GTGAGCACAA                                                    20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 8:

TGCTGAGAGT ACCCAGATGC                                                    20

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 9:

GATGGCCACA CCCACGCCC                                                     19

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 10:

TGCATGGAGA AGGTGCAGGC                                                    20

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 11:

CCTCTTGCCC ACCCTGACTGA                                                   21

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

TTCACACCAT TCTCCTGCCT                                                   20

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

AGTCCTCCCT GCTGCTGTGT G                                                 21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

TCAGTCAGGG TGGGCAAGAG G                                                 21

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 15:

GAGGAGCACC CCGTGCTGCT GA                                                22

(2) INFORMATION FOR SEQ ID NO: 16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 16:

CTAGAAGCAT TTGCGGTGGA CGATGGAGGG GCC                                    33

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 17:

TTGTAACCAA CTGGGACGAT ATGG                                              24

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear -continued (xi) SEQUENCE DESCRIPTION: SEQ ID NO: 18:

| | |
|---|---|
| GTCTTGATCT TCATGGTGCT AGG | 23 |

(2) INFORMATION FOR SEQ ID NO: 19:

(i) SEQUENCE CHARACTERISTICS:
        (A) LENGTH: 1624 base pairs
        (B) TYPE: nucleic acid
        (C) STRANDEDNESS: single
        (D) TOPOLOGY: linear (xi) SEQUENCE DESCRIPTION: SEQ ID NO: 19:

| | |
|---|---|
| CCGACTGAGG CACGAGCGGG TGACGCTGGG CCTGCAGCGC | 40 |
| GGAGCAGAAA GCAGAACCCG CAGAGTCCTC CCTGCTGCTG | 80 |
| TGTGGACGAC ACGTGGGCAC AGGCAGAAGT GGGCCCTGTG | 120 |
| ACCAGCTGCA CTGGTTTCGT GGAAGGAAGC TCCAGGACTG | 160 |
| GCGGGATGGG CTCAGCCTGT ATCAAAGTCA CCAAATACTT | 200 |
| TCTCTTCCTC TTCAACTTGA TCTTCTTTAT CCTGGGCGCA | 240 |
| GTGATCCTGG GCTTCGGGGT GTGGATCCTG GCCGACAAGA | 280 |
| GCAGTTTCAT CTCTGTCCTG CAAACCTCCT CCAGCTCGCT | 320 |
| TAGGATGGGG GCCTATGTCT TCATCGGCGT GGGGGCAGTC | 360 |
| ACTATGCTCA TGGGCTTCCT GGGCTGCATC GGCGCCGTCA | 400 |
| ACGAGGTCCG CTGCCTGCTG GGGCTGTACT TTGCTTTCCT | 440 |
| GCTCCTGATC CTCATTGCCC AGGTGACGGC CGGGGCCCTC | 480 |
| TTCTACTTCA ACATGGGCAA GCTGAAGCAG GAGATGGGCG | 520 |
| GCATCGTGAC TGAGCTCATT CGAGACTACA ACAGCAGTCG | 560 |
| CGAGGACAGC CTGCAGGATG CCTGGGACTA CGTGCAGGCT | 600 |
| CAGGTGAAGT GCTGCGGCTG GGTCAGCTTC TACAACTGGA | 640 |
| CAGACAACGC TGAGCTCATG AATCGCCCTG AGGTCACCTA | 680 |
| CCCCTGTTCC TGCGAAGTCA AGGGGGAAGA GGACAACAGC | 720 |
| CTTTCTGTGA GGAAGGGCTT CTGCGAGGCC CCCGGCAACA | 760 |
| GGACCCAGAG TGGCAACCAC CCTGAGGACT GGCCTGTGTA | 800 |
| CCAGGAGGGC TGCATGGAGA AGGTGCAGGC GTGGCTGCAG | 840 |
| GAGAACCTGG GCATCATCCT CGGCGTGGGC GTGGGTGTGG | 880 |
| CCATCATCGA GCTCCTGGGG ATGGTCCTGT CCATCTGCTT | 920 |
| GTGCCGGCAC GTCCATTCCG AAGACTACAG CAAGGTCCCC | 960 |
| AAGTACTGAG GCAGCTGCTA TCCCCATCTC CCTGCCTGGC | 1000 |
| CCCCAACCTC AGGGCTCCCA GGGGTCTCCC TGGCTCCCTC | 1040 |
| CTCCAGGCCT GCCTCCCACT TCACTGCGAA GACCCTCTTG | 1080 |
| CCCACCCTGA CTGAAAGTAG GGGGCTTTCT GGGGCCTAGC | 1120 |
| GATCTCTCCT GGCCTATCCG CTGCCAGCCT TGAGCCCTGG | 1160 |
| CTGTTCTGTG GTTCCTCTGC TCACCGCCCA TCAGGGTTCT | 1200 |
| CTTATCAACT CAGAGAAAAA TGCTCCCCAC AGCGTCCCTG | 1240 |
| GCGCAGGTGG GCTGGACTTC TACCTGCCCT CAAGGGTGTG | 1280 |

-continued

```
TATATTGTAT AGGGGCAACT GTATGAAAAA TTGGGGAGGA          1320

GGGGGCCGGG CGCGGTGCTC ACGCCTGTAA TCCCAGCACT          1360

TTGGAGGCC GAGGCGGGTG GATCACGAGG TCAGGAGATC           1400

GAGACCATCC TGGCTAACAT GGTGAAACCC CGTCTCTACT          1440

AAAAATACAA AAAAAATTTA GCCGGGCGCG GTGGCGGGCA          1480

CCTGTAGTCC CAGCTACTTG GGAGGCTGAG GCAGGAGAAT          1520

GGTGTGAACC CGGGAGCGGA GGTTGCAGTG AGCTGAGATC          1560

GTGCTACTGC ACTCCAGCCT GGGGGACAGA AAGAGACTCC          1600

GTCTCAAAAA AAAAAAAAAA AAAA                          1624
```

(2) INFORMATION FOR SEQ ID NO: 20:

(i) SEQUENCE CHARACTERISTICS:
  (A) LENGTH: 267 amino acids
  (B) TYPE: amino acid
  (C) STRANDEDNESS: unknown
  (D) TOPOLOGY: unknown (xi) SEQUENCE DESCRIPTION: SEQ ID NO: 20:

```
Met Gly Ser Ala Cys Ile Lys Val Thr Lys Tyr Phe
 1               5                  10

Leu Phe Leu Phe Asn Leu Ile Phe Phe Ile Leu Gly
         15                  20

Ala Val Ile Leu Gly Phe Gly Val Trp Ile Leu Ala
 25                  30                      35

Asp Lys Ser Ser Phe Ile Ser Val Leu Gln Thr Ser
             40                  45

Ser Ser Ser Leu Arg Met Gly Ala Tyr Val Phe Ile
 50                  55                      60

Gly Val Gly Ala Val Thr Met Leu Met Gly Phe Leu
                     65                  70

Gly Cys Ile Gly Ala Val Asn Glu Val Arg Cys Leu
     75                  80

Leu Gly Leu Tyr Phe Ala Phe Leu Leu Leu Ile Leu
 85                  90                      95

Ile Ala Gln Val Thr Ala Gly Ala Leu Phe Tyr Phe
                 100                 105

Asn Met Gly Lys Leu Lys Gln Glu Met Gly Gly Ile
     110                 115                 120

Val Thr Glu Leu Ile Arg Asp Tyr Asn Ser Ser Arg
                 125                 130

Glu Asp Ser Leu Gln Asp Ala Trp Asp Tyr Val Gln
         135                 140

Ala Gln Val Lys Cys Cys Gly Trp Val Ser Phe Tyr
145                 150                 155

Asn Trp Thr Asp Asn Ala Glu Leu Met Asn Arg Pro
                 160                 165

Glu Val Thr Tyr Pro Cys Ser Cys Glu Val Lys Gly
         170                 175                 180

Glu Glu Asp Asn Ser Leu Ser Val Arg Lys Gly Phe
                 185                 190

Cys Glu Ala Pro Gly Asn Arg Thr Gln Ser Gly Asn
     195                 200
```

```
His Pro Glu Asp Trp Pro Val Tyr Gln Glu Gly Cys
205                 210                 215

Met Glu Lys Val Gln Ala Trp Leu Gln Glu Asn Leu
            220                 225

Gly Ile Ile Leu Gly Val Gly Val Gly Val Ala Ile
        230                 235             240

Ile Glu Leu Leu Gly Met Val Leu Ser Ile Cys Leu
                245                 250

Cys Arg His Val His Ser Glu Asp Tyr Ser Lys Val
        255                 260

Pro Lys Tyr
265
```